United States Patent
Lamb

(10) Patent No.: US 7,172,573 B1
(45) Date of Patent: Feb. 6, 2007

(54) DEVICE FOR DEPOSITING A NON-FLOWABLE OBJECT OR A NON-FLOWABLE MEDICAMENT IN A BODY CAVITY

(76) Inventor: Peter James Brian Lamb, 12 Clifford Avenue, 1675 Irene (ZA)

( * ) Notice: Subject to any disclaimer, the term of this patent is extended or adjusted under 35 U.S.C. 154(b) by 0 days.

(21) Appl. No.: 10/031,860

(22) PCT Filed: Apr. 26, 2000

(86) PCT No.: PCT/IB00/00530
§ 371 (c)(1),
(2), (4) Date: Apr. 16, 2002

(87) PCT Pub. No.: WO00/66213

PCT Pub. Date: Nov. 9, 2000

(30) Foreign Application Priority Data
Apr. 29, 1999 (ZA) .................................... 99/3006

(51) Int. Cl.
*A61M 31/00* (2006.01)
*A61F 13/32* (2006.01)
(52) U.S. Cl. ...................... 604/59; 604/15; 604/11; 604/60
(58) Field of Classification Search ................ 604/150, 604/11–18, 59–60, 285–288, 904, 385.17, 604/275, 279, 123, 126, 124–125; 424/430–432; 514/534, 302; 206/529; D24/141; 600/29
See application file for complete search history.

(56) References Cited

U.S. PATENT DOCUMENTS

| 61,417 | A | * | 1/1867 | Grant ........................... 604/14 |
| 726,460 | A | * | 4/1903 | Reid ............................ 604/15 |
| 1,224,735 | A | * | 5/1917 | Gamache, Jr. et al. ......... 604/15 |
| 2,007,626 | A | * | 7/1935 | Waring ......................... 604/59 |

(Continued)

FOREIGN PATENT DOCUMENTS

DE       522 404       4/1931

(Continued)

*Primary Examiner*—Tatyana Zalukaeva
*Assistant Examiner*—Keshia Gibson
(74) *Attorney, Agent, or Firm*—Woodcock Washburn LLP

(57) ABSTRACT

A device (100) for depositing a non-flowable object or a non-flowable medicament in a body cavity includes an elongate body (12) which includes an elongate barrel (14) with a passage (18), configured to receive a non-flowable object or medicament, extending through the body (12). The passage (18) has an outlet (22) at a free end of the barrel (14), a portion of the passage (18) being curved. The device (10) also includes an ejector or plunger (30) which can be displaced along the passage (18) to push a non-flowable object or medicament received in the passage (18) out of the passage (18) through the outlet (22) thereof.

19 Claims, 2 Drawing Sheets

U.S. PATENT DOCUMENTS

| | | | |
|---|---|---|---|
| 2,882,900 A * | 4/1959 | Holter | 604/59 |
| 3,830,236 A * | 8/1974 | Hanke | 604/14 |
| 4,769,011 A | 9/1988 | Swaniger | 604/218 |
| 5,158,535 A * | 10/1992 | Paul et al. | 604/15 |
| 5,314,464 A | 5/1994 | KenKnight et al. | 607/132 |
| 5,395,308 A * | 3/1995 | Fox et al. | 604/15 |
| 5,397,312 A * | 3/1995 | Rademaker et al. | 604/218 |
| 6,190,348 B1 * | 2/2001 | Tiemann et al. | 604/15 |
| 6,248,089 B1 * | 6/2001 | Porat | 604/17 |
| 6,352,513 B1 * | 3/2002 | Anderson et al. | 600/572 |
| D457,627 S * | 5/2002 | Lamb | D24/141 |
| 6,537,260 B1 * | 3/2003 | Lamb | 604/279 |
| 6,652,513 B2 * | 11/2003 | Panescu et al. | 606/34 |
| 2004/0236265 A1 * | 11/2004 | Lamb | 604/11 |

FOREIGN PATENT DOCUMENTS

| | | |
|---|---|---|
| EP | 1 040 808 A2 | 10/2000 |
| EP | 1 040 808 A3 | 10/2000 |
| GB | 2 033 754 | 5/1980 |

* cited by examiner

DEVICE FOR DEPOSITING A NON-FLOWABLE OBJECT OR A NON-FLOWABLE MEDICAMENT IN A BODY CAVITY

This invention relates to a device of depositing a non-flowable object or a non-flowable medicament in a body cavity.

Various conventional devices for depositing a non-flowable medicament or object, such as a tablet in body cavities, such as the vagina and rectum, exist. Typically, these conventional devices comprise a blunt, straight, hollow tube or barrel into which a plunger or piston or ejector can be inserted from one end, with a medicament or object chamber being provided at an opposed end. GB 2 033 754 provides an example of such a device for inserting a sanitary tampon. The device of GB 2 033 754 includes a linear, circular cylindrical barrel with a blunt, rounded outlet end. DE 522 404 discloses an instrument for the introduction of radium needles into body orifices or tissue. The instrument of DE 522 404 may include a curved or bent barrel with the curvature being located between an outlet of the barrel and a gripping portion of the device. However, the device of DE 522 404 is not suitable for the self-introduction of non-flowable medicaments such as tablets, capsules, suppositories, pills, bougies, or the like in the vagina of a female user, nor is it suitable for the self-insertion of a tampon in the vagina of a female user.

All of the conventional devices suffer from at least some of the following problems: The conventional device is of a hard and non-pliable material so there is no bend or give during insertion of the device into a vagina. This rigidity makes vaginal insertion more difficult and painful. Often women do not know that the vagina is angled upwards from its opening and that it is not horizontal. After inserting a leading end of the conventional device through the vaginal opening in the horizontal direction, the leading end collides with the back wall of the vagina, which is painful and causes the user to think that the device has reached the limit of the vagina. The user then deposits the medicament or object at a too shallow depth in the vagina. No stop guard is provided to limit the depth of insertion of the conventional devices into the vagina. If the device is inserted to the full depth of the vagina and collides with the vaginal vault, considerable pain is caused. This lack of depth control is particularly hazardous in the case of a pregnant women. Some conventional devices have leading ends which flare outwards which make them even more difficult to insert into a vagina. Conventional devices can only comfortably be inserted into a vagina when the women is lying on her back with her knees flexed. It is difficult to insert conventional devices which are often difficult to grip and difficult to control when being inserted into a vagina.

It is an object of the present to provide means which alleviate at least some of these problems.

According to a first aspect of the invention, there is provided a device for use by a female user to self-deposit a non-flowable object or a non-flowable medicament in her vagina, the device including:

an elongate body which includes a gripping portion and an analogous barrel extending from the gripping portion, with a passage, configured to receive a non-flowable object or medicament, extending through the body, the passage having an outlet at a free end of the barrel and a portion of the passage, located in the gripping portion, being curved in the longitudinal direction of the passage; and an ejector or plunger which can be displaced by the user along the passage to push a non-flowable object or medicament received in the passage out of the passage through the outlet thread into the vagina of the user.

According to a second aspect of the invention, there is provided a tampon insertion device which includes:

an elongate body which includes an elongate barrel with a passage, configured to receive a tampon, extending through the body, the passage having an outlet at a free end of the barrel and a portion of the passage spaced from the outlet being curved in the longitudinal direction of the passage; and an ejector or plunger which can be displaced along the passage to push a tampon received in the passage out of the passage through the outlet thereof.

The barrel may be penile-shaped at least in cross section.

According to a third aspect of the invention, there is provided a device for use by a female user to self-deposit a non-flowable object or a non-flowable medicament in her vagina, the device including an elongate body which includes an elongate barrel which is penile-shaped or roughly triangular in cross section with a passage, configured to receive a non-flowable object of medicament, extending through the body, the passage having an outlet at a frame end of the barrel, a portion of the passage spaced from the outlet being curved in the longitudinal direction of the passage; and an ejector or plunger which can be displaced by the user along the passage to push a non-flowable object or medicament received in the passage out of the passage through the outlet thereof into the vagina of the user.

In this specification, the term "non-flowable medicament" is intended to include tablets, capsules, suppositories, pills, bougies, or the like.

The passage is typically round or circular in cross-section.

The passage may have an inlet remote from its outlet. The curved portion of the passage may render a centrally disposed longitudinal axis of the barrel and a centrally disposed axis through the inlet of the passage at an obtuse angle relative to each other. The obtuse angle may be between 170° and 135.° Preferably, the obtuse angle is between 160° and 140°, and most preferably between 155° and 145°, and is thus selected to correct for vaginal inclination.

The body of the device according to the second and third aspects of the invention may also include a gripping portion from which the barrel extends. The inlet of the passage may thus be in the gripping portion, which may be thickened compared to the barrel, thus also functioning in use as a stop formation, limiting the length of the body of the device which may be introduced into a body cavity.

The curved portion of the passage of the device according to the second and third aspects of the invention is also typically located in the gripping portion of the body, so that the portion of the passage in the barrel is typically linear, allowing at least a portion of the barrel to be straight. Preferably, the entire barrel is straight, which is an advantage, since the human vagina is straight and not curved.

An outlet end portion of the barrel may have the general shape or may incorporate at least some of the design features of the glans penis. Thus, the barrel may have a rounded point which flares back like the content of a glans penis and which in use lifts the opposing vaginal walls apart when the barrel is inserted into a vagina by a wedging action. The roughly triangular cross-section of the barrel, similar to that of a penis, allows the smallest area of contact or friction with a posterior vaginal wall. Side walls of the barrel are thus in use angled away from lateral walls of the vagina, with a relatively broad superior wall of the barrel being stabilized by low pressure contact with the anterior vaginal wall.

The ejector or plunger may have a flexible rod, allowing the rod to bend to follow the curvature of the passage when it is displaced along the passage. The rod may be of a synthetic plastics or polymetric material, such as polypropylene or the like.

The passage may include a medicament or object chamber for receiving the non-flowable medicament or object. The chamber may be spaced from the outlet of the passage, allowing a part of the barrel, above the outlet, and a part of the barrel, below the outlet, to be displaced or forced towards each other when the barrel is being inserted into a body cavity, thus at least partially closing off the outlet whilst the barrel is being inserted into the body cavity and preventing the object or medicament from scraping against or injuring body tissue material, such as the vaginal mucosa.

At least the barrel may be of a material having a Shore A hardness between 40 and 80, e.g. 70. Thus, the barrel may be of a synthetic plastics or polymeric material, such as silicone rubber, having a suitable hardness. The gripping portion may be of a thermoplastic material, with the barrel and the gripping portion being moulded or fused together. Instead, the barrel and the gripping portion may be fitted together by other means, such as glue or mechanical attachment means or control combi moulding, thus advantageously allowing the gripping portion to be of a thermoplastic material which has a lower maximum working temperature than the moulding temperature of the material of which the barrel is formed, and which may thus be cheaper. In another embodiment of the invention, the gripping portion and the barrel may both be of the same synthetic or polymeric plastics material, e.g. silicone rubber, the body of the device thus being monolithic and integrally moulded. Instead, the body and the ejector or plunger may be manufactured from paper or paper pulp, rendering the device disposable. The material may be selected to be biodegradable or to allow the devices to be flushed safety down a toilet.

The barrel may have a length of between 60 mm and 100 mm, e.g. 70 mm and a maximum external diameter of between 10 mm and 20 mm, e.g. 17 mm, when the device is intended for a non-flowable medicament.

The outlet of the passage may be in the form of a slit extending between opposed sides of the barrel and may be located on the longitudinal axis of the barrel.

The body may define gripping surfaces such that the body can be gripped between a thumb, and index finger and a middle finger of one hand of a user. The gripping surfaces may be arranged such that when the body is being held between the tree fingers, with the middle finger and the index finger touching the body in respective areas and the body being orientated such that said areas are in the same horizontal plane, the barrel projects upwardly away from said horizontal plane at an angle between 45° and 10°.

The passage may be shaped and dimensioned to receive a tampon. The barrel may thus include a longitudinally extending slit through which a string of the tampon received in the passage can protrude.

In one embodiment of the invention, the slit may extend from the outlet and may form a right angle at an end of a longitudinally extending portion thereof remote from the outlet to extend transversely across an upper surface of the barrel. An upper front portion of the barrel is thereby rendered displaceable in flip top fashion. This allows insertion of a solid object such as a tampon into the barrel from above, without having to feed the solid object into the barrel through the outlet.

The ejector or plunger may include a thumb grip at a free end of its rod, the gripping portion of the body defining a recess for the thumb grip so that almost all of the ejector or plunger can be received inside the body of the device when the ejector or plunger is pushed as far into the passage as it can go.

The invention will now be described, by way of example, with reference to the accompanying diagrammatic drawings in which FIG. 1 is a sectional side view of an embodiment of a device in accordance with the invention for depositing a non-flowable medicament in a body cavity;

Figure 1:
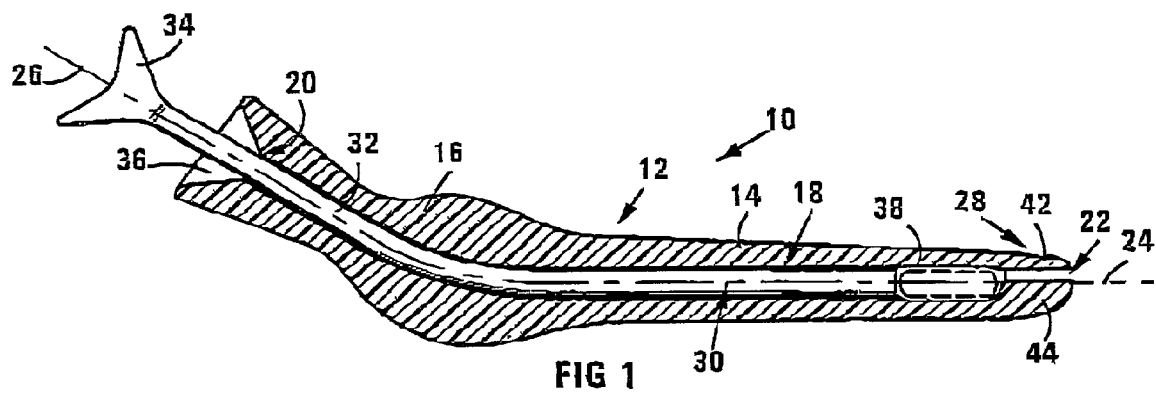
Figure 2:
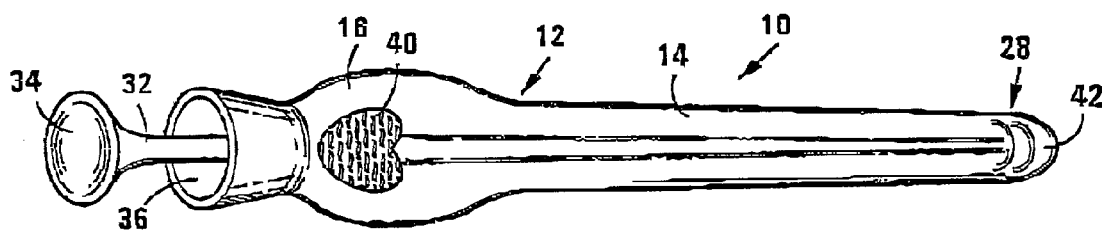
FIG. 2 is a top plan view of the device of FIG. 1.
Figure 3:
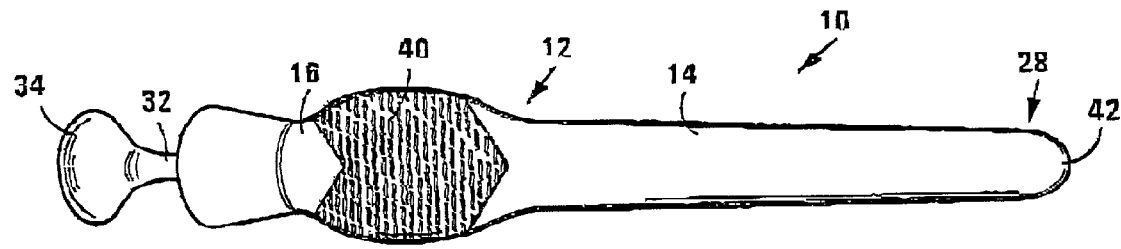
FIG. 3 is a bottom plan view of the device of FIG. 1.
Figure 4:
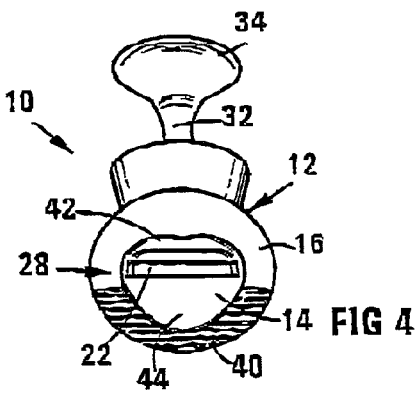
FIG. 4 is a front end view of the device of FIG. 1.
Figure 5:
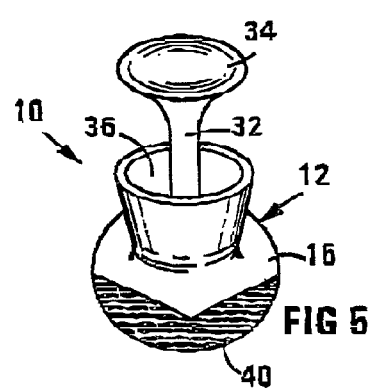
FIG. 5 is a rear end view of the device of FIG. 1.
Figure 6:
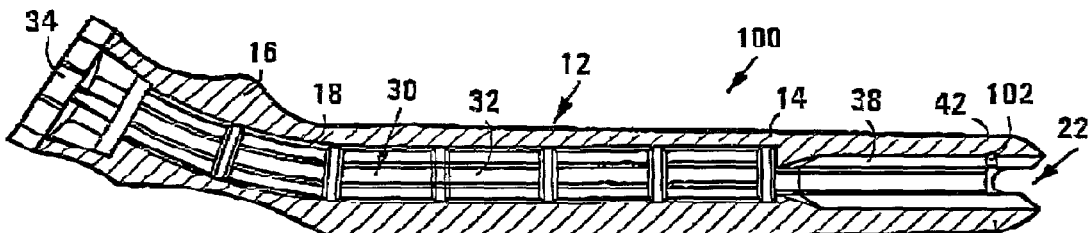
FIG. 6 is a sectional side view of another embodiment of a device in accordance with the invention for depositing a non-flowable medicament or a non-flowable object in a body cavity.
Figure 7:
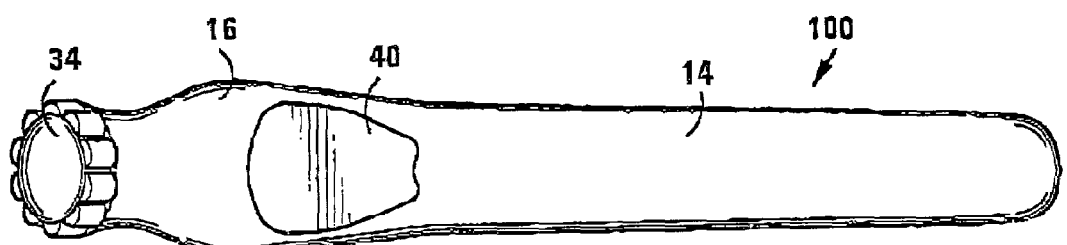
FIG. 7 is a top plan view of the device of FIG. 6.
Figure 8:
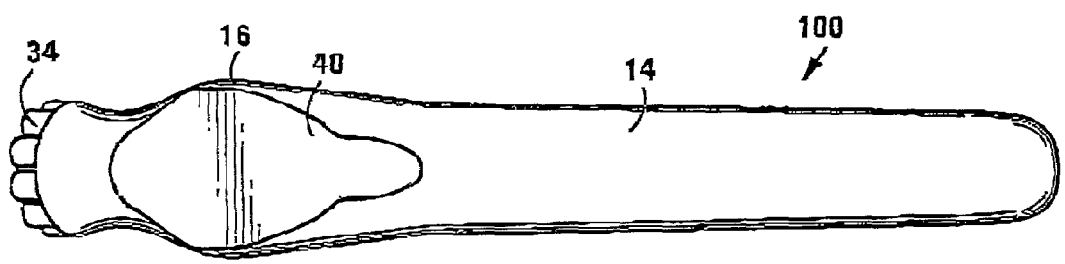
FIG. 8 is a bottom plan view of the device of FIG. 6.
Figure 9:
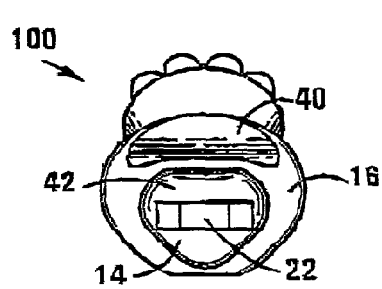
FIG. 9 is a front end view of the device of FIG. 6.
Figure 10:
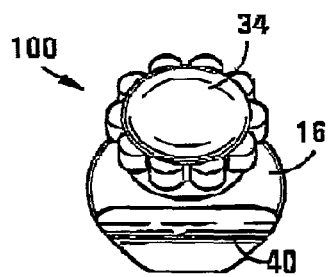
FIG. 10 is a rear end view of the device of FIG. 6.

Referring to FIGS. 1 to 5 of the drawings, reference numeral 10 generally indicates an embodiment of a device in accordance with the invention for depositing a non-flowable medicament or object in a body cavity, such as a vagina. The device 10 includes an elongate monolithic body 12 which comprises an elongate barrel 14 and a gripping portion 16 from which the barrel 14 extends.

The barrel 14 and the gripping portion 16 are integrally moulded from a synthetic plastics or polymeric material such as a silicone rubber and has a Shore A hardness of about 70. A passage 18 extends through the gripping portion 16 and the barrel 14. The passage 18 has an inlet 20 in the gripping portion 16 and an outlet 22 at a free end of the barrel 14, remote from the gripping portion 16. A portion of the passage 18 between the inlet and the outlet and located in the gripping portion 16, is curved in side view, as can be clearly seen in FIG. 1 of the drawings. The passage 18 is round in cross-section.

The curved portion of the passage 18 between the inlet 20 and its outlet 22 renders a centrally disposed longitudinal axis 24 of the barrel 14 and a centrally disposed axis 26 through the inlet 20 of the passage 18, at an obtuse angle of 150° relative to each other (see FIG. 1), and this angle thus matches the angle of inclination of the vagina of a standing women relative to the horizontal.

The barrel 14 is generally penile shaped and is thus roughly triangular in cross-section, similar to the cross section of the penis. More accurately, a cross-sectional outline of the barrel 14 falls on the outline of a triangle. An outlet end portion 28 of the barrel 14, remote from the gripping portion 18, generally has the shape of a glans penis. A bottom surface of the end portion 28 has a sled-like curve in side view to inhibit abrasion of the posterior vaginal wall in use. The barrel 14 thus has a rounded point which flares back like the corona of a glans penis and which in use lifts and wedges the opposing vaginal walls apart when the barrel 14 is inserted into a vagina.

The outlet 22 of the passage 18 is in the form of a slit extending between opposed sides of the barrel 14 and is located in an upper half of the outlet end portion 28, to avoid scraping vaginal exudate into the outlet 22 during insertion of the barrel 14 into a vagina in use.

The device 10 includes a piston or ejector or plunger 30 which can be displaced along the passage 18 and which includes a flexible rod 32 of polypropylene. The rod 32 is thus able to follow the curvature of the passage 18 when the plunger 30 is displaced along the passage 18. The plunger 30 includes an ergonometrically designed thumb grip 34 at a free end of the flexible rod 32. As can be clearly seen in FIG. 1 of the drawings, the gripping portion 16 of the body 12 defines a recess 36 for the thumb grip 34 so that almost all of the plunger 30 can be received inside the body 12 when the plunger 30 is pushed as far into the passage 18 as it can go.

The passage 18 includes or defines a medicament or object chamber 38 (see FIG. 1) for receiving the non-flowable medicament or non-flowable object. The chamber 38 is spaced from the outlet 22 of the passage and is in the form of a widening of the passage 18 tailored to receive a tablet or capsule or tampon or the like.

Roughened and depressed gripping surfaces 40 are provided on an external top surface and an external bottom surface of the gripping portion 16 of the body 12.

The barrel 14 is approximately 70 mm long and has a maximum external diameter at about 17 mm.

The device 10 is particularly, though not necessarily exclusively suitable for depositing a non-flowable medicament, such as a tablet or capsule, in a vagina. In use, the ejector or plunger 30 is withdrawn from the passage 18 at least far enough so that it does not protrude into the chamber 38, as shown in FIG. 1 of the drawings, and the non-flowable medicament is placed inside the medicament chamber by inserting it through the outlet 22. The barrel 14 is then inserted into a body cavity, such as the vagina of a human female until the gripping portion 16 limits the part or length of the body 12 of the device 10 which can be introduced into the vagina. Thus, the gripping portion 16 also functions in use as a stop formation. The gripping portion 16 affords a large comfortable grip for the hand of the person inserting the barrel 14 into the vagina.

As will be appreciated, since the body 12 is of a silicone rubber and thus quite flexible, a part or upper lip 42 of the barrel 14, above the outlet 22, and a part or lower lip 44 of the barrel 14, below the outlet 22 are displaced or forced towards each other whilst the barrel 14 is being inserted into the vagina. Thus, the outlet 22 is closed off whilst the barrel 14 is being inserted into the vagina, inhibiting intrusion of vaginal exudate into the passage 18 through the outlet 22. The flexibility of the lips 42, 44 also allows for easy insertion of the non-flowable medicament into the channel 38 and prevents abrasion or injury to the vaginal mucosa by a sharp-edged non-flowable medicament, e.g. a vaginal tablet.

By enlarging the barrel 14 and the chamber 38, the device 10 can also easily be adapted for use in inserting a tampon in a vagina. Typically, in such a case, the barrel 14 will include a longitudinally extending slit through which a string of the tampon can protrude.

When the barrel 14 is fully inserted into the vagina, the ejector or plunger 30 is pushed into the body 12 as far as it can go, forcing the non-flowable medicament or solid object out of the chamber 38, through the outlet 22, and thus depositing the non-flowable medicament or object in the vagina. The barrel 14 is then withdrawn from the vagina.

Referring to FIGS. 6 to 10 of the drawings, reference numeral 100 generally indicates another embodiment of a device in accordance with the invention for depositing a solid object, such as a non-flowable medicament or a non-flowable object, in a body cavity, such as a vagina. The device 100 is similar to the device 10, and unless otherwise indicated, the same parts or features are indicated by the same reference numerals used in relation to the device 10.

The body 12 of the device 100 is of Krayton G 2705 material having a Shore A hardness of 55. The ejector or plunger 30 is of the same material.

Unlike the outlet 22 of the device 10, the outlet 22 of the device 100 is located on a central longitudinal axis of the barrel 14 (not shown). Also unlike the device 10, the gripping portion 16 of the body 12 of the device 100 does not define a recess which can accommodate the thumb gain 34. Instead, when the ejector or plunger 30 is inserted fully into the passage 18, the thumb grip 34 abuts an end of the body 12 remote from the outlet 22.

The device 100 has a semi-circular 0.5 mm deep groove 102 in the upper lip 42 of the barrel 14. This facilitates bending of the upper lip 42 towards the lower lip 44 during insertion of the barrel 14 into a vagina thereby to close the outlet 22 off whilst the barrel 14 is being inserted into the body cavity. The groove 102 also facilitates the passage of a solid non-flowable object from the chamber 38 out through the outlet 22, by allowing the upper lip 42 to move way from the lower lip 44.

The device 100 is used in similar fashion to the device 10. It is to appreciated that, when the body 16 is gripped between a thumb, an index finger and a middle finger of one hand of a user, with the thumb touching the upper gripping surface 40 and the index finger and the middle finger touching the lower gripping surface 40, and with areas on the lower surface 40 touched by the middle finger and the index finger being oriented such that they are in the same horizontal plane, the barrel 14 projects upwardly away from the horizontal plane at an angle of about 30°. If a women holds the device 100 such that said areas touched by the middle and index finger are in line at an angle of about 120° to the horizontal, which is a natural holding position, the barrel 14 projects upwardly at an angle of about 150° relative to the horizontal, which is the angle of inclination of the vagina of a standing women relative to the horizontal, as hereinbefore mentioned.

The Applicant believes that the device 10, 100 as illustrated, and particularly when intended to deposit a non-flowable medicament such as a capsule or tablet, or a solid object such as a tampon, in a vagina, has the following advantages:

The length of the barrel 14 is not intimidating, but nonetheless provides effective depth of deposition of the non-flowable medicament or the object. The barrel 14 is of a relatively soft, elastic material which is less difficult and painful to insert than the barrel of conventional devices. The material is easier for the fingers to grip securely and the grippability of the device is further improved by the gripping surfaces 40. The generally triangular, penile-like cross-section of the barrel 14 (see FIG. 4) is easier and more comfortable to insert into a vagina. Friction against the back vagina wall is reduced.

The angular arrangement of the barrel 14 relative to the inlet 20 of the passage 18 promotes easier advancement of the barrel 14 up the vagina. There is a built-in correction for the direction or inclination of the vaginal cavity, which causes less damage and discomfort to the user. The barrel 14 can be inserted whilst the user is sitting or standing and the procedure is therefor much easier and more comfortable to accomplish physically and much less an effort to a female's dignity.

The glans penis-like outlet end portion 28 of the barrel 14 of the device 10 is easier and more comfortable to insert the leading end portions of conventional devices. The shape and location of the outlet 23 of the barrel 14 provides for better hygiene and promotes comfort when the barrel 14 is inserted into the vagina, by eliminating any scraping effect on the back wall of the vagina.

The thickened gripping portion 16 ensures automatic depth control when the barrel 14 is inserted into a vagina.

The integrally moulded design of the gripping portion 16 and the barrel 14 provides the device 10, 100 with a degree of flexibility, which enhances comfort and ease when the barrel 14 is inserted into a vagina.

The gripping portion 16 provides a large comfortable handle for the device 10. It affords a secure grip and therefor better control of the device 10 during insertion of the barrel 14 into the vagina.

The invention claimed is:

1. A device for use by a female user to self-deposit a solid object or a non-flowable medicament in her vagina, the device including
    an elongate body which includes a gripping portion and an elongate straight barrel extending from the gripping portion, with a passage, configured to receive a solid object or medicament, extending through the gripping portion and through the barrel, the gripping portion being thick relative to the barrel in at least one transverse dimension and forming a stop for insertion of the device;
    the passage having an outlet at a free end of the barrel and a portion of the passage, located in the gripping portion, being curved in the longitudinal direction of the passage and a portion of the passage, located in the barrel, being linear; and
    a flexible ejector or plunger which is slidingly located in the passage and which thus extends through the gripping portion and through the barrel, the flexible ejector being able to follow the curvature of the passage so that it can be displaced by the user along the passage to push a solid object or medicament received in the passage out of the passage through the outlet thereof in the vagina of the user.

2. A device as claimed in claim 1, in which the barrel is roughly triangular in a transverse cross section.

3. A device as claimed in claim 1, in which the passage has an inlet remote from its outlet and in which the curved portion of the passage renders a centrally disposed longitudinal axis of the barrel and a centrally disposed axis through the inlet of the passage at an obtuse angle of between 170° and 135° relative to each other.

4. A device as claimed in claim 3, in which the obtuse angle between the axis is between 160° and 140°.

5. A device as claimed in claim 1, in which an outlet end portion of the barrel has the general shape, or incorporates at least some of the design features of a glans penis.

6. A device as claimed in claim 1, in which the passage includes a medicament or object chamber for receiving the solid medicament or object.

7. A device as claimed in claim 6, in which the chamber is spaced from the outlet of the passage, allowing a part of the barrel, above the outlet, and a part of the barrel, below the outlet, to be displaced or forced towards each other when the barrel is being inserted into a vagina, thus at least partially closing off the outlet whilst the barrel is being inserted into the vagina and preventing the object or medicament from scraping against or injuring body tissue material.

8. A device as claimed in claim 1, in which at least the barrel is of a material having a Shore A hardness between 40 and 80.

9. A device as claimed in claim 1, in which the body and the ejector or plunger are manufactured from paper or paper pulp, rending the device disposable.

10. A device as claimed in claim 1, in which the body defines gripping surfaces such that the body can be gripped between a thumb, an index finger and a middle finger of one hand of a user, the gripping surfaces being arranged such that when the body is being held between the three fingers, with the middle finger and the index finger touching the body in respective areas and the body being orientated such that said areas are in the same horizontal plane, the barrel projects upwardly away from said horizontal plane at an angle of between 45° and 10°.

11. A device as claimed in claim 1, in which the body is a monolithic, integrally moulded body.

12. The device as claimed in claim 1, in which the gripping portion is bulbous.

13. The device as claimed in claim 1, in which the barrel is configured to receive a tampon.

14. A device for use by a female user to self-deposit a solid object or medicament in her vagina, the device including
    an elongate body which includes a gripping portion that forms a stop insertion of the device, an elongate barrel which is roughly triangular in a transverse cross section with a passage, configured to received a solid object or medicament, extending through the body, the passage having an outlet at a free end of the barrel, a portion of the passage spaced from the outlet being curved in the longitudinal direction of the passage; and
    an ejector or plunger which can be displaced by the user along the passage to push a solid object or medicament received in the passage out of the passage through the outlet thereof into the vagina of the user.

15. A tampon insertion device which includes
    an elongate body which includes a gripping portion and an elongated straight barrel extending from the gripping portion, with a passage, configured to receive a tampon, extending through the gripping portion and through the barrel, the gripping portion being thick relative to the barrel in at least one transverse dimension, the gripping portion being thick relative to the barrel in at least one transverse dimension, the passage having an outlet a free end of the barrel and a portion of the passage, located in the gripping portion, being curved in the longitudinal direction of the passage and a portion of the passage, located in the barrel, being linear; and
    a flexible ejector or plunger which is slidingly located in the passage and which thus extends through the gripping portion and through the barrel, the flexible ejector being able to follow the curvature of the passage so that it can be displaced along the passage to push a tampon received in the passage out of the passage through the outlet thereof.

16. A device as claimed in claim 15, in which the barrel includes a longitudinally extending slit through which a string of a tampon received in the passage can protrude.

17. A device as claimed in claim 15, in which a part of the barrel, above the outlet, and a part of the barrel, below the outlet, are displaceable towards each other, allowing the parts to be displaced or forced towards each other when the barrel is being inserted into vagina, thus at least partially closing off the outlet whilst the barrel is being inserted into the vagina and preventing the tampon from scraping against or injuring body tissue material.

18. A device for use by a female user to self-deposit a solid object or a non-flowable medicament in her vagina, the device including:
- a body including a gripping portion and an elongate straight barrel extending from the gripping portion, the gripping portion being configured to be gripped by the user with one hand, and forms a stop for insertion of the device;
- a passage, configured to receive a solid object or medicament, extending through the body, the passage having an outlet at a free end of the body;
  - a first portion of the passage, located in the gripping portion, being curved in the longitudinal direction of the passage,
  - a second portion of the passage, located in the barrel, being linear; and
- a flexible rod slidingly located in the passage and extending through the gripping portion and through the barrel,
- a thumb grip attached to the flexible rod and located opposite the free end of the body such that the pushing on the thumb grip by the user's thumb displaces the rod to push a solid object or medicament received in the passage out of the passage through the outlet thereof into the vagina of the user.

19. A device for use by a female user to self-deposit a solid object or a non-flowable medicament in her vagina, the device including:
- a body which includes a bulbous gripping portion and an elongate straight barrel extending from the gripping portion, wherein the gripping portion forms a stop for insertion of the device;
- a passage, configured to receive a solid object or medicament, extending through the body, the passage having an outlet at a free end of the barrel;
  - a first portion of the passage, located in the gripping portion, being curved in the longitudinal direction of the passage,
  - a second portion of the passage, located in the barrel, being linear; and
- a flexible ejector or plunger which is slidingly located in the passage and which thus extends through the gripping portion and through the barrel, the flexible ejector being able to follow the curvature of the passage so that it can be displaced by the user along the passage to push a solid object or medicament received in the passage out of the passage through the outlet thereof into the vagina of the user.

* * * * *